United States Patent [19]

Fugo

[11] Patent Number: 5,538,016
[45] Date of Patent: Jul. 23, 1996

[54] METHOD OF NON-INCISIONAL VISION ENHANCEMENT OF POSTOPERATIVE INCISIONAL KERATOREFRACTIVE SURGERY OF THE CORNEA

[76] Inventor: Richard J. Fugo, 1507 Plymouth Blvd., Norristown, Pa. 19401

[21] Appl. No.: 452,082

[22] Filed: May 26, 1995

[51] Int. Cl.$^6$ .................................................. A61B 19/00
[52] U.S. Cl. .......................................... 128/898; 606/166
[58] Field of Search ............................ 606/166; 128/898

[56] References Cited

PUBLICATIONS

Gayton, Johnny, author; Gilbert, M., editor. Refractive Keratotomy Enhancements: A Systematic Approach. Eyecare technology Magazine, vol. 5, No. 1, pp. 50–53, Jan./Feb. 1995.

Waring, G..Refractive Keratotomy, Repeated Surgery for Residual Myopia and Hyperopia After Refractive Surgery. pp. 641–667, , 1992 Mosby Yearbook.

*Primary Examiner*—Gary Jackson
*Assistant Examiner*—Mark S. Leonardo

[57] ABSTRACT

A method of reopening healing or healed corneal incision lines by applying pressure to the front surface of the cornea and thereby creating a physical shearing force on cornea incision lines which tear the incision lines open. A blunt micro-ophthalmic probe is used, and does not encroach upon the deep base of the original corneal incision cavity. The blunt probe does not cut or incise any virgin, healthy cornea tissue or remove any healing connective tissue from within the cavity of the original corneal incision. Each time that the healing or healed incision line is reopened, the body secretes additional healing connective tissue which is added to or coats the original connective tissue wedge of wound "healing tissue" inside of the corneal cavity of the original keratorefractive incision. The thicker that the wedge of connective tissue between the walls of the incision line becomes, the more the walls of the original corneal incision line are physically separated by this connective tissue wedge. By repeatedly reopening the original keratorefractive incision line, an increased thickness in the connective tissue wedge may be slowly produced in a titrated fashion. As we progressively separate the original walls of the corneal incision lines, a progressive steepening of the peripheral cornea with a concomitant progressive flattening of the central cornea is induced. Likewise, a progressive decrease in corneal astigmatism may be induced. In this way, we may repeat this procedure until we have effectively neutralized the overall optical refractive error of the eye and thereby minimize or even eliminate the need for eyeglass or contact lens wear.

7 Claims, No Drawings

METHOD OF NON-INCISIONAL VISION ENHANCEMENT OF POSTOPERATIVE INCISIONAL KERATOREFRACTIVE SURGERY OF THE CORNEA

BACKGROUND—FIELD OF INVENTION

This invention relates to improving vision in post-operative incisional keratorefractive surgery of the cornea of the eye, specifically to a method of non-incisional vision improvement by a technique of reopening the healing or healed incisions in the cornea without using a sharp, cutting instrument; wherein use of blunt mechanical manipulation of the keratorefractive incision lines in the cornea produce a realignment in the position of the keratorefractive incision line walls and a resulting change in the topographical contour of the cornea surface.

BACKGROUND—DESCRIPTION OF PRIOR ART

Keratorefractive eye surgeons place incisions in the front surface of the eye in procedures such as Radial Keratotomy and Astigmatic Keratotomy. Radial Keratotomy is a surgical procedure wherein incisions are placed in the front surface of the cornea of the eye in order to minimize or eliminate myopia or nearsightedness whereas Astigmatic Keratotomy is a surgical procedure wherein surgical incisions are placed in the front surface of the cornea of the eye in order to minimize or eliminate irregularities in the shape of the corneal surface known as corneal astigmatism. These Keratorefractive incisions are placed in the peripheral and midperipheral portions of the cornea only. The closer that these incisions extend toward the center of the cornea, the greater is the chance that severe visual distortion may occur. Keratorefractive techniques are well established procedures in the field of ophthalmology. The incisions that are placed in the front surface of the cornea in Radial Keratotomy and Astigmatic Keratotomy are custom designed for each cornea from numerous formulas that have been developed by physicians since these procedures were first used in the late 19th century. The custom design of each of these surgeries includes the location of the incision, the depth of each incision and the length of each incision. Parenthetically, the goal for the width of each incision is to create a cutting path that is as thin as possible which is why Keratorefractive surgeons have discarded metal blades in favor of high precision diamond blades since diamond blades are more than five times thinner in width than metal blades. Following Keratorefractive surgery, as the incisions in the cornea heal, they produce a change in the surface contour or shape of the cornea. The goal of the eye surgeon is to place planned incisions in the cornea that will produce a change in the shape of the cornea such that the refractive error of the overall optical system of the eye is minimized. When the refractive error of the eye is minimized, the light rays that enter the front surface of the eye are focused through the optical system of the eye onto the retina of the eye, in which case the need for eyeglasses or contact lens is progressively decreased wherein as the refractive error continues to decrease no eyeglasses or contact lenses will eventually be needed for the eye to see clearly. In the event that the healing corneal incisions of Keratorefractive Surgery provide an inadequate change in the shape of the cornea and thereby an inadequate improvement in the refractive error of the eye, the eye will still require eyeglasses or contact lenses in order to see clearly. In these cases, the surgeon may attempt to alter the healing pattern of the keratorefractive corneal incisions with various combinations of ophthalmic topical eye medications such as ophthalmic pilocarpine drops or ointment, ophthalmic steroid drops or ointment, ophthalmic hypertonic drops or ointment or ophthalmic lubricant drops or ointment. The effect of these medications on the post-keratorefractive eye is very unpredictable and unreliable, therefore these medications frequently do not sufficiently alter the healing pattern in the corneal incisions such that the final refractive error in the overall refractive system of the eye is not minimized significantly, accordingly, the eye will still require eyeglasses or contact lenses in order to see clearly. The eye surgeon will then frequently choose to recut the originally placed corneal incisions or even add new incisions on the front surface of the cornea in an attempt to allow the incisions to heal again in a more desirable manner such that they will produce a change in the shape or contour of the cornea which will more closely reflect the desired cornea surface topography change anticipated by the eye surgeon as defined by their preoperative keratorefractive plan based on calculations derived from established keratorefractive formulas. If the anticipated change in the corneal surface topography is achieved, then the refractive error of the overall refractive system of the eye is more effectively neutralized such that the eye would no longer need eyeglasses or contact lenses to see clearly.

All previous methods to recut the healing or healed corneal incisions of incisional keratorefractive surgery involves placing a topical anesthetic agent on the front surface of the eye. Following this, the surgeon then forces a probe into the healing tissue between the two walls of the original corneal incision. This probe is placed into the base of the incision cavity and then used as a device to pry open the healing or healed corneal incisions as well as clean out all cellular products present in the original corneal incision cavity including cellular healing tissue. This placement of the microinstrument probe into the original incision cavity has been believed by eye surgeons to inadequately open the healing or healed incisions, whereby in all previous techniques the main purpose of this initial step is to identify and delineate the original initial corneal incision tract and also to clean as much material as possible from the original Keratorefractive incision tract including epithelial cells and newly formed connective tissue generated by the bodies own healing process. In all previous protocols, the initial step of reopening the original corneal incision is thereby followed by a second step which requires the eye surgeon to use a sharp blade such as a diamond blade to incise the healing tissue between the original incision tissue walls for the entire length of the original corneal incision and at times to even extend the length of the original incision into virgin, uncut corneal tissue in the direction towards the center of the pupil of the eye. Furthermore, the surgeon sometimes places additional new incisions into the front surface of the cornea in order to further neutralize residual refractive error.

All previous techniques to reopen previously placed keratorefractive incisions of the cornea, to surgically increase the length of the original keratorefractive incisions in the cornea, and to surgically add additional incisions in the front surface of the cornea heretofore known suffer from a number of disadvantages:

(a) When a probe is forced into the base of the cavity between the incision walls, contaminants and foreign material on the surface of the cornea and in the tear film may be forced into the base of the incision cavity and thereby contaminate the entire cavity between the original incision walls. If this contaminant contains a microbial pathogen, then this creates a nidus for intracorneal infection. Non-living contaminants present a nidus for intracorneal inflammation with millions of macrophage cells from outside of the cornea migrating into the cornea to the contaminant site in order to degrade the contaminant then ingesting a small piece of the contaminant and subsequently migrating out of the cornea in an attempt to remove the contaminant from the cornea;

(b) The surgical step of using a sharp cutting blade to attempt to recut the entire original keratorefractive incision cavity suffers from poor control of precisely where on the cornea the blade incises and exactly what portion of the cornea the blade incises. The cutting blade usually drifts out of the original incision cavity and into the walls of the original incision cavity. Along the original corneal incision line, the cutting blade often drifts into one wall of the original incision cavity then back into the cavity of the original incision then often drifts into the opposite wall of the original incision cavity. This type of uncontrolled cutting action results in a destruction of normal, healthy corneal tissue with an uncontrolled, irregular scarring of corneal tissue. These uncontrolled incisions in the cornea result in a grossly uncontrolled, widened and irregular scarring of the cornea which can result in severe disfigurement of the cornea, increased corneal astigmatism and increased weakness in the strength of the cornea. The increased disfigurement in the cornea may be of such magnitude that irregular bands of corneal scar tissue may be visible to the naked eye of an observer thereby presenting a cosmetically unacceptable scar on the eye of the keratorefractive patient. Increased corneal astigmatism can result in an increased dependency on eyeglasses or contact lenses which is what the original corneal surgery attempted to correct. If the induced astigmatism of the cornea were to become excessive, then the clarity of vision in the eye may be significantly reduced even when wearing eyeglasses or contact lenses. Increased weakness in the strength of the cornea can result in an increased susceptibility of the eye to rupture in the event that the eye should sustain a direct blow or trauma.

During the recutting maneuver in all previous techniques to improve the results of keratorefractive surgery, the cutting blade may also incise out of control into the base of the original incision cavity to the extent that it may actually perforate through the entire cornea and enter into the inner cavity of the eye, thereby representing a perforation of the eyeball. This perforation may require a technically difficult surgical suturing or surgical suture closure of the gaped perforated opening through the eyeball. This perforation represents a potential contamination site for pathogenic organisms to be introduced from outside the eyeball to inside the eyeball which may result in a severe infection inside the eyeball known as Infectious Endophthalmitis, which may require intense antibiotic therapy including injection of antibiotic into the eyeball, hospitalization, extensive intraocular surgery to remove growing pockets of infectious waste from inside of the eye, and even the need to surgically remove the eyeball.

Stress placed on any surface of the body may create a potential effect on a healing incision line in that body surface. However, eye surgeons and ophthalmologists have not believed that one may completely reopen or realign in a repeatable fashion an entire healing or healed keratorefractive incision line in the cornea by applying a blunt stress or pressure on the surface of the cornea or a shearing stress placed on the incision cavity walls of the original keratorefractive incision line without severely damaging the eye itself. Ophthalmologists have also not believed that it is possible to completely reopen or realign keratorefractive incisions by placing a blunt device in the outer portion of the keratorefractive incision cavity and using this probe to create a shearing force that can effectively strip open the entire original keratorefractive incision, even down to the base of the incision. For these reasons, all prior keratorefractive protocols employ techniques that penetrate the original corneal incision cavity with a probe or instrument and utilize these probes or instruments to crack the healing or healed incision open and as an excavating utensil to dredge the base of the corneal incision cavity in order to scrape all of the contents of the original keratorefractive cavity to the surface of the cornea. In this way, prior protocols have attempted to utilize microinstrument probes to clean out all contents from the original radial keratotomy or astigmatic keratotomy incision line cavity in the cornea. All prior keratorefractive protocols also employ a sharp, cutting blade to attempt to cut open the original healing or healed corneal incision lines by attempting to cut through the plane of healing tissue in the cavity of the original corneal incision, though the blade will inevitably stray in an uncontrolled fashion into virgin, healthy corneal tissue along the walls or base of the original corneal incision cavity;

(c) When an original radial corneal incision line is extended in length, the direction of the extension of the length of the line is toward the center of the cornea. The closer that the incision lines approach the very center of the cornea, the higher is the risk for the patient to develop distortion of vision.

(d) When additional corneal incision lines are placed in the front surface of the cornea, additional normal corneal tissue is damaged and there is an increased risk for the surgeon to perforate the eyeball.

SUMMARY OF THE INVENTION

My invention is a method employing blunt stress to the corneal tissue of the eye in order to completely reopen the original keratorefractive lines without recutting the cornea. Instead of previously used incisional techniques, blunt mechanical manipulation of the keratorefractive incision lines in the cornea allows one to produce a realignment in the position of the two incision line walls which will allow the peripheral cornea to further steepen and thereby produce a stretching force on the central cornea or adjacent cornea which produces a further flattening of the central cornea and/or reduction in corneal astigmatism. By slowly and deliberately titrating the apposition of the corneal incision walls along each corneal incision line, one may titrate the degree of flattening of the central cornea and thereby titrate a progressive decrease in the refractive error in the keratorefractive operative eye without recutting corneal tissue with a blade.

When the cornea is incised, this stimulates a reaction wherein a wound healing connective tissue is secreted into the incision cavity by normal body healing mechanisms. This wound healing process occurs anywhere that body tissue sustains a cut. This wound healing tissue has a high viscosity and therefore is "sticky" to touch which is why it is referred to as "tissue glue". This highly viscous "tissue glue" allows us to realign the original incision walls and hold them in place as the healing process develops and evolves.

Prior RK protocols advise cleaning out or complete removal of this connective healing "tissue glue" from the original corneal incision cavity. My invention teaches away from this prior approach and instead teaches not to remove the normal healing "tissue glue" which is present in the original corneal incision cavity. My invention teaches that the healing connective tissue present in the incision cavity should not be removed from the incision cavity. If the surgeon wishes to further neutralize residual refractive error in the eye in order to further improve the uncorrected vision in that eye then the highly viscous healing tissue known as "tissue glue" is the adhesive material that allows us to realign the original corneal incision line without having to place further incisions into the cornea. Over the course of several weeks, these wedges of "tissue glue" in the original corneal wound incisions are infiltrated with fibroblast healing cells which secrete collagen protein fibers into the "tissue glue" wedge thereby converting the early viscous "tissue glue" wedge into a progressively stronger wedge of healing connective tissue that permanently holds the original cornea incision walls in the desired alignment which produces excellent vision without glasses. Exact alignment of the keratorefractive incision walls causes a steepening of the peripheral cornea which in turn stretches the central cornea and causes it to flatten. By flattening the central cornea, we are able to modify the refractive or light bending power of the eye and therefore control the overall focusing power of the eye such that light rays entering the eye through the cornea are better focused on the retina without the need of contact lenses or eyeglasses.

Briefly and basically, in accordance with the present invention, a method of reopening healing or healed incisions on the cornea of the eye includes the steps of placing a topical ophthalmic anesthetic on the eye. The cornea of the eye is visualized with a microscope and the corneal incisions that had been previously placed during an incisional keratorefractive session are examined. A blunt, non-cutting probe is forcefully applanated against the front surface of the cornea thereby flattening the normal convex external surface of the cornea. The blunt probe may be placed over the top of the healing or healed incision line on the front surface of the cornea or may be placed immediately adjacent to a healing or healed incision line on the front surface of the cornea. As the probe is pushed inward against the external surface of the cornea, one is able to visualize with the microscope that the healing or healed incision lines begin to progressively gape or split open. With the microscope, one is able to visualize healing tissue inside the original incision line begin to strip off of the original incision walls. The corneal compression maneuvers on the front surface of the cornea as described above are repeated until one visualizes wide gaping of the healing or healed corneal incision lines with strands of healing tissue between the original corneal incision walls proceed to peel off of the walls of the incision cavity. The gaping of the corneal incision lines with stripping of tissue strands from the walls of the original corneal incisions is produced by a shearing stress which is generated by progressively deforming the dome shape of the cornea. This shearing stress creates a tearing or ripping force along the healing or healed incision lines in the cornea. An additional approach to non-incisional enhancement of keratorefractive surgery is to place an angled tip of any generic ophthalmic probe into the original healing keratorefractive incision cavity. The angulation and the thickness of the probe are nonspecific but a fine probe with a diameter of about 25 gauge to 30 gauge in thickness is acceptable. The tip of the probe is used to exert a shearing force on the original incision cavity walls sufficient to strip open the original keratorefractive incision line. The tip of the probe is kept in the outer one half of the incision cavity thereby minimizing the risk of inoculating the base of the incision with contaminating substances and also minimizing the risk of blunt trauma to the deeper portion of the walls and the base of the original incision line which potentially could result in an inadvertent perforation of the eyeball. Since the original corneal incision line is once again completely open, the walls of the keratorefractive incision may be realigned with highly viscous normal healing "tissue glue" with the creation of wedges of connective tissue in the original incision cavity. My technique teaches away from all previous techniques of improving post-operative incisional keratorefractive vision which teach to reopen the original corneal incisions and remove all tissue and material deposited in the original incision cavity including corneal epithelial cells and connective tissue, as well as cutting virgin corneal tissue.

On the contrary, my invention of non-incisional vision enhancement of post-operative incisional keratorefractive surgery of the cornea teaches not to incise virgin corneal tissue and not to remove the cellular healing tissue laid down by the cornea during its normal healing process.

During the initial healing phase following an incision of the cornea, the outer epithelial cells of the cornea slide into the cornea incision cavity and the body secretes highly viscous healing tissue known as "tissue glue" into the incision. Since the epithelial cells and highly viscous "tissue glue" form an adhesive plug that temporarily holds the incision walls together, the bodies healing mechanisms are triggered in order to form a progressively stronger bond or connection between the incised corneal incision walls. Cells within the body such as fibroblasts which are devoted to the healing process will secrete specific substances such as collagen fibrils into the original incision cavity which will bind and permanently connect the original incision walls together and thereby replace the initial adhesive healing plug. This strong incision connecting material is called "connective tissue". Connective tissue acts as a natural tissue glue and is a complex substance including collagen fibrils embedded in a gel-like matrix known as "ground substance". Ground substance is composed of numerous molecules including mucopolysaccharides.

Each time that the original incision line is again broken open, the healing mechanisms of the body are stimulated to secrete more connective tissue along the incision walls. The newly secreted healing tissue binds to the old wedge of connective tissue in the original corneal incision cavity, thereby increasing the thickness of the composite connective tissue wedge. The new connective tissue acts as a tissue glue that allows one to stabilize and realign the incision walls each time they are broken open in a blunt fashion. Each time the incision lines are broken apart, new connective tissue is produced and is added to the previous wedge of connective tissue. Therefore, each time the incision line is broken open, the wedge of connective tissue between the original incision walls is microscopically increased in thickness whereby these changes in connective tissue wedge thicknesses may be appreciated only by examining the connective tissue wedges with a microscope. Moreover, the thicker that the overall wedge of connective tissue becomes between the original keratorefractive incision walls, the wider that the original keratorefractive incision walls are spread apart precisely because of the progressively thicker connective tissue wedge positioned between the original keratorefractive incision walls. As we progressively spread apart the original incision walls with progressively thicker plugs of connective tissue, we increase the circumference of the peripheral cornea and thereby progressively produce a steepening of the peripheral cornea with a concomitant progressive flattening of the central cornea and/or reduction in corneal astigmatism. By titrating the thickness of the connective tissue wedge in the original keratorefractive incision cavity, we may titrate the degree of flattening of the central cornea and the degree of neutralization of cornea irregularity known as astigmatism such that we may titrate a progressive improvement in the vision of the eye.

Following sessions of repeated corneal compression and/or corneal incision line cleavage with blunt probes under microscopic guidance, the original corneal incisions will again be opened and again be allowed to heal in the manner anticipated by the surgeon and thereby produce a change in the shape or contour of the cornea that more closely reflects the desired corneal topography anticipated by the eye surgeon. In this case, the refractive error of the overall refractive system of the eye is more effectively neutralized such that the eye will no longer need eyeglasses or contact lenses to see clearly.

ADVANTAGES

Accordingly, the advantages of this present invention are:

(a) to provide a non-incisional method of permanently improving vision following incisional keratorefractive surgery to eliminate the need to wear contact lenses or eyeglasses with a method that is less dangerous than all previous keratorefractive enhancement techniques, that is less stressful than all previous kerato enhancement techniques, that is less time consuming and less disruptive to a patient's daily schedule than previous keratorefractive enhancement techniques, and that is more cost effective than previous keratorefractive enhancement techniques;

(b) to provide a method of reopening healing or healed incisions in the cornea of the eye without having to place a probe, device, or instrument down into the bottom or base of the original incision cavity thereby minimizing the risk of introduction of contaminant and foreign material from the surface of the cornea and in the tear film. This will minimize the risk of inoculation of pathogenic microbes into the base of the incision cavity thereby minimizing the creation of a nidus for intracorneal infection. This method also minimizes the risk of introducing non-living contaminants into the base of the corneal incision cavity thereby eliminating a potential inflammatory nidus in the structure of the cornea wherein millions of macrophage cells from outside of the cornea would be stimulated to migrate through corneal tissue and to the non-living contaminant site in the contaminated incision cavity of the cornea in order to degrade and remove the contaminant from the cornea.

(c) to provide a method of reopening healing or healed incisions in the cornea without having to place a sharp cutting blade into the original corneal incision cavity thereby eliminating the possibility of having the cutting blade drift out of the original incision cavity and into the walls of the incision cavity. The incision blade often drifts in an uncontrolled fashion from one incision wall back to the original incision cavity then into the incision wall on the other side of the original incision cavity. My method thereby eliminates this type of uncontrolled cutting action of the sharp cutting blade placed into the original corneal incision cavity, thereby eliminating the subsequent destruction of normal, healthy corneal tissue with a grossly widened and irregular scarring of corneal tissue. My method thereby eliminates an uncontrolled, grossly widened, and irregular band of scarring of the cornea which can result in severe disfigurement of the cornea, increased corneal astigmatism, and increased weakness in the strength of the cornea. My method therefore eliminates the formation of uncontrolled, excessively thickened, irregular bands of corneal scar tissue which may be seen by the naked eye of an observer thereby presenting a cosmetically unacceptable scar on the eye. My method also eliminates the risk of producing increased corneal astigmatism while recutting the original corneal incisions with a sharp blade which would result in an increased dependency on eyeglasses or contact lenses which the original corneal surgery attempted to correct. My method also eliminates the possibility of induction of excessive astigmatism of the cornea by the sharp cutting blade in which case the clarity of vision in the eye would be significantly reduced even when wearing eyeglasses or contact lenses. My method also eliminates the increased weakening in the strength of the cornea which may result from damage to normal corneal tissue in the walls of the original corneal incision cavity which may be produced by a cutting blade attempting to cut open the healing or healed corneal incision. My method therefore eliminates this increased corneal weakness produced by recutting the original corneal incision and thereby eliminates the increased susceptibility of rupturing the eyeball should the eye sustain a direct blow or trauma.

(d) to provide a method that also eliminates the possibility of the cutting blade during the recutting maneuver from incising out of control into the base of the original incision cavity to the extent that it may actually perforate through the entire cornea and enter into the inner cavities of the eye, thereby representing a perforation of the eyeball. Such a perforation may require a technically difficult suturing or suture closure of the gaped opening through the eyeball. Such a perforation would represent a potential contamination site for pathogenic organisms to be introduced inside the eyeball which may result in a severe infection inside the eyeball known as Infectious Endophthalmitis which could require intense antibiotic therapy including injection of antibiotic into the eyeball, hospitalization, extensive intraocular surgery to remove growing pockets of infectious waste from inside the eye and even the need to surgically remove the eye.

DETAILED DESCRIPTION OF THE PREFERRED EMBODIMENTS

My method of non-incisional vision enhancement of post-operative incisional keratorefractive surgery of the cornea is different from all previous techniques used by eye surgeons. All previous techniques utilize probes that are forced deeply into the base of the original incision cavity and then used as a wedge to pry open the healing or healed corneal incision lines. These probes are then used to remove and extract all cellular products of the normal healing process including epithelial cells, connective tissue, and healing tissue from between the original incision walls. This maneuver is then followed by placing a sharp cutting blade into the original corneal incision cavity and incising the healing or healed incision open. Contrary to previous techniques, my method of permanently improving the vision of an eye following incisional keratorefractive surgery is performed by placing blunt force on the front surface of the cornea by pushing inward with a blunt probe that is applanated against the external surface of the cornea while examining the cornea and the incisions of the cornea with direct microscopic observations. This maneuver is repeated until the gape in the corneal incision is clinically acceptable to the eye surgeon who is monitoring the procedure with microscopic guidance. Pressure is applied against the front surface of the cornea with a blunt probe. This blunt pressure against the front surface of the cornea is applied in a fashion such that corneal tissue is not pushed inward with a magnitude that would cause corneal tissue to cross the imaginary plane that is created by the limbus of the eye. The limbus of the eye is the point on the eye where the clear cornea meets the white sclera of the eye. The limbus of the eye runs 360 degrees around the periphery and extreme margin of the cornea of the eye. An additional maneuver in my new technique is to reopen healing keratorefractive incisions in the cornea by placing an angled, blunt, non-cutting tip of any generic blunt ophthalmic probe into the healing incision cavity. The angulation and the thickness of the blunt probe is non-specific but a thin non-cutting probe with a thickness of about 25 gauge to about 30 gauge is acceptable. The tip of the probe is kept in the external or outer one half of the incision cavity, thereby minimizing the risk of inoculation with contaminating substances of the deep base portion of the original keratorefractive incision and also minimizing the risk of blunt trauma to the deeper portions of the original incision cavity, which potentially could result in an inadvertent perforation of the eyeball. By using this blunt, non-cutting tip as a hook to place a pulling force on the external margins of the incision line, a shearing force is created which may strip open the entire original keratorefractive incision line. Accordingly, the reader will see that my method of reopening healing or healed corneal incisions allows for a more efficient and safer method and technique than previous methods and techniques to perform modifications to the original keratorefractive surgery in order to improve the vision of the eye without the assistance of eyeglasses and contact lenses. Furthermore, my method of reopening healing or healed incisions on the cornea has the additional advantages in that it provides;

a quicker, more efficient and safer method of reopening healing or healed incisions on the cornea;

a method that allows an eye surgeon to use blunt manipulation of corneal incisions to realign the original corneal incision walls by creating a controlled production of progressively thicker wedges of corneal healing connective tissue in the original incision cavity which will concomitantly produce a progressive flattening of the central cornea with a titratable, progressive decrease in the refractive error in the optical system of the eye;

a method that eliminates blunt trauma to the lower portion of the walls and base of the original corneal incision cavity;

a method that minimizes the risk of introducing contaminates into the base of the original incision cavity;

a method that minimizes the risk of creating inflammatory sites in the incisional cavities secondary to the introduction of non-living contaminants into the base of the incision cavity;

a method that minimizes the risk of creating an intracorneal nidus of infection secondary to the introduction of infectious living contaminants into the base of the incisional cavity;

a method of minimizing the risk of perforating through the entire thickness of the cornea and thereby creating an open channel through which contaminants may pass from the outside of the eye into the inside of the eye;

a method of minimizing the risk of Endophthalmitis with the serious potential of intense antibiotic therapy including injection of antibiotic into the eye, intense surgery to remove infectious waste from within the eye, hospitalization, and even the need to surgically remove the eye;

a method of minimizing the risk of incising and damaging virgin, healthy corneal tissue in the lower walls of the original corneal incision cavity;

a method of minimizing cosmetically unacceptable scars on the surface of the cornea since the increase in the thickness of the connective tissue wedges in the original keratorefractive incision cavity produced by my technique are microscopic and can only be visualized with the assistance of a high power microscope and cannot be visualized with the naked eye;

a method of minimizing the creation of excess astigmatism of the cornea due to damage of virgin healthy corneal tissue in the walls of the corneal incision cavity;

a method of minimizing the risk of increased dependency on eyeglasses and contact lenses as a result of tissue damage to the original corneal incision walls;

a method of minimizing the risk of not being able to improve the clarity of vision even with eyeglasses or contact lenses because of excessive astigmatism as a result of excessive corneal tissue damage to the original corneal keratorefractive incision walls which may occur from previous techniques;

a method of minimizing the risk of producing high levels or even intolerable levels of glare from light which is scattered off of and distorted by large corneal scars created by previous incisional vision enhancement techniques, resulting from repeatedly cutting the cornea a second, third, or fourth time;

Although the description above contains many specificities, these should not be construed as limiting the scope of the invention, but as merely providing illustrations of some of the presently preferred embodiments of this invention. Thus, the scope of the invention should be determined by the appended claims and their legal equivalents rather than the examples given.

I claim:

1. A method of improving the postoperative visual acuity outcome of incisional keratorefractive surgery of a cornea, comprising the steps of:

(a) irrigating topical anesthesia onto the outer surface of said cornea and conjunctiva in order to anesthetize the eyeball (b) observing said cornea with a lens system that will magnify and improve visualization of said cornea and the incisions in said cornea (c) reopening healing or healed keratorefractive incisions in said cornea by compressing the external surface of said cornea with a blunt probe with sufficient force to indent the convex outer surface of said cornea (d) reopening healing or healed keratorefractive incisions in said cornea by placing the end or active tip of said blunt probe into the upper half of a keratorefractive incision cavity and inducing a shearing force that will strip open entire said keratorefractive incision cavity.

2. The method of claim 1 wherein a blunt force on the external surface of said cornea or in said external portion of said original corneal incision cavity is transformed into said shearing force that will physically tear open said healing or healed corneal incision of said keratorefractive surgery, thereby creating said cavity in said original corneal keratorefractive incision.

3. The method of claim 1 wherein no healing connective tissue is removed from said original reopened keratorefractive incision, whereas said highly viscous healing connective tissue is utilized to realign said original keratorefractive incision under microscopic guidance and said healing connective tissue may be allowed to accumulate in said original keratorefractive incision cavity.

4. The method of claim 1 that will allow said natural healing connective tissue to be secreted into said original keratorefractive cavity in said cornea creating a physical wedge of said connective tissue which may be intentionally thickened by repeatedly reopening said original healing or healed keratorefractive incision and thereby stimulating said cornea tissue to secrete additional said healing, connective tissue into said original corneal incision cavity wherein it accumulates.

5. The method of claim 1 wherein said progressively thickened wedges of said normal healing connective tissue in said original keratorefractive incision cavity will allow a controlled separation of said original keratorefractive corneal incision and a controlled widening of said cavity between said original keratorefractive incision walls.

6. The method of claim 1 wherein increasing the thickness of said connective tissue wedge in said keratorefractive incision produces a planned progressive gape in said original keratorefractive incision line walls resulting in a progressive flattening of the central cornea and/or reduction in astigmatism.

7. The method of claim 1 wherein said keratorefractive incisions are reopened and realigned repeatedly until the corneal refractive power is altered to a point at which clear vision in the operated eye is achieved without the need for eyeglasses or contact lenses.

* * * * *